United States Patent
Tanaka et al.

(10) Patent No.: US 10,058,386 B2
(45) Date of Patent: Aug. 28, 2018

(54) MICROWAVE PROVIDING DEVICE AND MICROWAVE SURGICAL DEVICE PROVIDED WITH SAME

(71) Applicant: ALFRESA PHARMA CORPORATION, Osaka (JP)

(72) Inventors: Masatoshi Tanaka, Fukuoka (JP); Yoshinori Kohara, Chiba (JP); Masahide Okada, Chiba (JP)

(73) Assignee: ALFRESA PHARMA CORPORATION, Osaka (JP)

(*) Notice: Subject to any disclaimer, the term of this patent is extended or adjusted under 35 U.S.C. 154(b) by 326 days.

(21) Appl. No.: 14/784,687

(22) PCT Filed: Oct. 17, 2013

(86) PCT No.: PCT/JP2013/006179
§ 371 (c)(1),
(2) Date: Oct. 15, 2015

(87) PCT Pub. No.: WO2014/174556
PCT Pub. Date: Oct. 30, 2014

(65) Prior Publication Data
US 2016/0074115 A1    Mar. 17, 2016

(30) Foreign Application Priority Data
Apr. 26, 2013 (JP) .................. 2013-093729

(51) Int. Cl.
*A61B 18/18* (2006.01)
*A61B 18/00* (2006.01)

(52) U.S. Cl.
CPC .......... *A61B 18/1815* (2013.01); *A61B 2018/00589* (2013.01); *A61B 2018/00702* (2013.01); *A61B 2018/1823* (2013.01)

(58) Field of Classification Search
CPC ...... A61B 18/1815; A61B 2018/00589; A61B 2018/00702; A61B 2018/1823
See application file for complete search history.

(56) References Cited

U.S. PATENT DOCUMENTS

2008/0319434 A1* 12/2008 Rick .................. A61B 18/18
606/33
2010/0082024 A1   4/2010 Brannan et al.
(Continued)

FOREIGN PATENT DOCUMENTS

JP     2510475      4/1996
JP     2009-528     1/2009
(Continued)

OTHER PUBLICATIONS

International Search Report dated Nov. 19, 2013 in International (PCT) Application No. PCT/JP2013/006179, with English translation.

*Primary Examiner* — Michael Peffley
*Assistant Examiner* — Amanda Zink
(74) *Attorney, Agent, or Firm* — Wenderoth, Lind & Ponack, L.L.P.

(57) ABSTRACT

A microwave providing device is provided, which is capable of effectively extending the coagulation range of a treatment target tissue by setting the conditions for intermittently providing microwaves. An output controller controls a microwave generator based on a first efficiency of dielectric heating by microwaves with respect to a cumulative radiation period of microwaves radiated intermittently to a treatment target tissue S and a second efficiency of dielectric heating by microwaves with respect to a cumulative radiation period of microwaves radiated continuously to the treatment target tissue so that microwaves are intermittently radiated at least after a reference cumulative radiation period (Continued)

that is set in advance as a cumulative radiation period at which the first efficiency becomes larger than the second efficiency.

8 Claims, 8 Drawing Sheets

(56) References Cited

U.S. PATENT DOCUMENTS

| | | |
|---|---|---|
| 2010/0100092 A1* | 4/2010 | Turner ................... A61B 18/18 606/33 |
| 2010/0125269 A1 | 5/2010 | Emmons et al. |
| 2010/0137857 A1 | 6/2010 | Shroff et al. |
| 2011/0098695 A1 | 4/2011 | Brannan |
| 2012/0259330 A1* | 10/2012 | Tani ................... A61B 18/1815 606/45 |
| 2014/0052124 A1 | 2/2014 | Brannan |
| 2015/0126991 A1 | 5/2015 | Brannan |
| 2015/0223886 A1 | 8/2015 | Rick et al. |

FOREIGN PATENT DOCUMENTS

| | | |
|---|---|---|
| JP | 2010-82460 | 4/2010 |
| JP | 2011-92715 | 5/2011 |
| JP | 2012-506300 | 3/2012 |
| WO | 2011/081196 | 7/2011 |

\* cited by examiner

FIG.4

| SAMPLE NO. | RADIATION PERIOD(s) | PAUSE PERIOD(s) | NUMBER OF REPEATS | TOTAL RADIATION PERIOD(s) | TOTAL PAUSE PERIOD(s) | TOTAL PERIOD(s) | MEASURED COAGULATION VALUE(mm) W×D |
|---|---|---|---|---|---|---|---|
| EXAMPLE 1 | 10 | 5 | 9 | 90 | 40 | 130 | 21×45 |
| EXAMPLE 2 | 10 | 5 | 12 | 120 | 55 | 175 | 24×45 |
| EXAMPLE 3 | 10 | 5 | 21 | 210 | 100 | 310 | 32×50 |
| EXAMPLE 4 | 20 | 5 | 5 | 100 | 20 | 120 | 20×35 |
| EXAMPLE 5 | 20 | 5 | 8 | 160 | 35 | 195 | 23×45 |
| EXAMPLE 6 | 20 | 5 | 11 | 220 | 50 | 270 | 28×50 |
| EXAMPLE 7 | 10 | 10 | 12 | 120 | 110 | 230 | 23×45 |
| EXAMPLE 8 | 15 | 10 | 8 | 120 | 70 | 190 | 26×45 |
| EXAMPLE 9 | 20 | 10 | 6 | 120 | 50 | 170 | 26×50 |

FIG.5

| SAMPLE NO. | RADIATION PERIOD(s) | PAUSE PERIOD(s) | NUMBER OF REPEATS | TOTAL RADIATION PERIOD(s) | TOTAL PAUSE PERIOD(s) | TOTAL PERIOD(s) | MEASURED COAGULATION VALUE(mm) W×D |
|---|---|---|---|---|---|---|---|
| COMPARATIVE EXAMPLE 1 | 60 | 0 | 0 | 60 | 0 | 60 | 15×35 |
| COMPARATIVE EXAMPLE 2 | 10 | 5 | 6 | 60 | 25 | 85 | 15×20 |
| COMPARATIVE EXAMPLE 3 | 15 | 5 | 4 | 60 | 15 | 75 | 14×30 |
| EXAMPLE 10 | 10 | 5 | 10 | 100 | 45 | 145 | 22×40 |
| EXAMPLE 11 | 15 | 10 | 10 | 150 | 90 | 240 | 21×40 |
| EXAMPLE 12 | 10 | 5 | 15 | 150 | 70 | 220 | 20×40 |
| EXAMPLE 13 | 15 | 10 | 15 | 225 | 140 | 365 | 28×50 |
| EXAMPLE 14 | 10 | 5 | 20 | 200 | 95 | 295 | 28×45 |
| EXAMPLE 15 | 15 | 10 | 20 | 300 | 190 | 490 | 25×45 |
| EXAMPLE 16 | 10 | 5 | 25 | 250 | 120 | 370 | 33×55 |
| EXAMPLE 17 | 15 | 10 | 25 | 375 | 240 | 615 | 31×60 |
| EXAMPLE 18 | 10 | 5 | 30 | 300 | 145 | 445 | 31×55 |
| EXAMPLE 19 | 10 | 5 | 35 | 350 | 170 | 520 | 35×50 |

FIG.6

| MEASURED COAGULATION VALUE(mm) W×D | 35×50 | 33×55 | 31×60 | 31×55 | 28×50 | 28×45 | 25×45 | 22×40 | 21×40 | 20×40 | 15×35 | 15×20 | 14×30 |
|---|---|---|---|---|---|---|---|---|---|---|---|---|---|
| SAMPLE NO. | EXAMPLE 19 | EXAMPLE 16 | EXAMPLE 17 | EXAMPLE 18 | EXAMPLE 13 | EXAMPLE 14 | EXAMPLE 15 | EXAMPLE 10 | EXAMPLE 11 | EXAMPLE 12 | COMPARATIVE EXAMPLE 1 | COMPARATIVE EXAMPLE 2 | COMPARATIVE EXAMPLE 3 |
| RADIATION PERIOD(s) | 10 | 10 | 15 | 10 | 15 | 10 | 15 | 10 | 15 | 10 | 60 | 10 | 15 |
| TOTAL RADIATION PERIOD(s) | 350 | 250 | 375 | 300 | 225 | 200 | 300 | 100 | 150 | 150 | 60 | 60 | 60 |
| PAUSE PERIOD(s) | 5 | 5 | 10 | 5 | 10 | 5 | 10 | 5 | 10 | 5 | 0 | 5 | 5 |
| TOTAL PAUSE PERIOD(s) | 170 | 120 | 240 | 145 | 140 | 95 | 190 | 45 | 90 | 70 | 0 | 25 | 15 |
| TOTAL PERIOD(s) | 520 | 370 | 615 | 445 | 365 | 295 | 490 | 145 | 240 | 220 | 60 | 85 | 75 |
| NUMBER OF REPEATS | 35 | 25 | 25 | 30 | 15 | 20 | 20 | 10 | 10 | 15 | 0 | 6 | 4 |

FIG.7

| SAMPLE NO. | RADIATION PERIOD(s) | PAUSE PERIOD(s) | NUMBER OF REPEATS | TOTAL RADIATION PERIOD(s) | TOTAL PAUSE PERIOD(s) | TOTAL PERIOD(s) | MEASURED COAGULATION VALUE(mm) W×D |
|---|---|---|---|---|---|---|---|
| EXAMPLE 20 | 10 | 5 | 30 | 300 | 145 | 445 | 30×60 |
| EXAMPLE 21 | 10 | 10 | 30 | 300 | 290 | 590 | 28×55 |
| EXAMPLE 22 | 10 | 15 | 30 | 300 | 435 | 735 | 26×47 |
| EXAMPLE 23 | 90 / 10 | 5 | 90×1 / 10×21 | 300 | 105 | 405 | 30×52 |

MICROWAVE PROVIDING DEVICE AND MICROWAVE SURGICAL DEVICE PROVIDED WITH SAME

TECHNICAL FIELD

The present invention relates to a microwave providing device for providing microwaves for realizing hemostasis, coagulation, excision, or the like of a treatment target tissue, such as a biological tissue subject to treatment, to a surgical electrode and a microwave surgical device provided with the same.

BACKGROUND ART

In the related art, a microwave surgical device for realizing hemostasis, coagulation, excision, or the like of a tumor tissue such as a liver cancer, for example, by radiating thermal energy generated by dielectric heating of microwaves to a treatment target tissue via a needle-shaped surgical electrode is known.

Here, thermal energy generated by dielectric heating of microwaves is mainly generated by dielectric loss of moisture having relatively high relative permittivity in a treatment target tissue.

Thus, if microwaves are continuously radiated to a treatment target tissue, after coagulation of the treatment target tissue progresses to some extent, the moisture in the treatment target tissue around a surgical electrode becomes insufficient, spark discharge occurs between the surgical electrode and the treatment target tissue, and the treatment target tissue carbonizes. In this case, a coagulation range (the range indicated by symbol W in FIG. 9) of the treatment target tissue extending around the surgical electrode cannot be extended to a required range.

Thus, as disclosed in Patent Literature 1, for example, a technique of intermittently providing microwaves to a surgical electrode in order to repeating dielectric heating while suppressing a decrease in the moisture in a treatment target tissue is known.

However, in the microwave surgical device disclosed in Patent Literature 1, since specific conditions for intermittently providing microwaves are not specified, the coagulation range of the treatment target tissue cannot be extended effectively.

CITATION LIST

Patent Literature

Patent Literature 1: Japanese Patent No. 2510475

SUMMARY OF INVENTION

An object of the present invention is to provide a microwave providing device capable of effectively extending the coagulation range of a treatment target tissue by setting the conditions for intermittently providing microwaves and to provide a microwave surgical device provided with the same.

In order to solve the problem, the present inventors have invented the present invention by focusing on the fact that first efficiency of dielectric heating by microwaves with respect to a cumulative radiation period of the microwaves intermittently radiated to a treatment target tissue exceeds second efficiency of dielectric heating by microwaves with respect to a cumulative radiation period of microwaves continuously radiated to the treatment target tissue when the cumulative radiation period exceeds a specific period.

Specifically, the present invention provides a microwave providing device for providing microwaves to a surgical electrode, including: a microwave generator that generates the microwaves; and an output controller that controls the microwave generator so that the microwaves are generated intermittently, wherein the output controller controls the microwave generator based on a first efficiency of dielectric heating by microwaves with respect to a cumulative radiation period of microwaves radiated intermittently to a treatment target tissue and a second efficiency of dielectric heating by microwaves with respect to a cumulative radiation period of microwaves radiated continuously to the treatment target tissue so that microwaves are intermittently radiated at least after a reference cumulative radiation period that is set in advance as a cumulative radiation period at which the first efficiency becomes larger than the second efficiency.

Moreover, the present invention provides a microwave surgical device including: a surgical electrode; and the microwave providing device for supplying microwaves to the electrode.

According to the present invention, it is possible to effectively extend the coagulation range of a treatment target tissue by setting the conditions for intermittently providing microwaves.

BRIEF DESCRIPTION OF DRAWINGS

FIG. 4 is a table illustrating test result 1 obtained using the test device of FIG. 3.

FIG. 5 is a table illustrating test result 2 obtained using the test device of FIG. 3.

FIG. 6 illustrates test result 2 of FIG. 5 in descending order of the coagulation ranges.

FIG. 7 is a table illustrating test result 3 obtained using the test device of FIG. 3.

DESCRIPTION OF EMBODIMENTS

Hereinafter, an embodiment of the present invention will be described with reference to the accompanying drawings. The following embodiment is an example in which the present invention is embodied but is not intended to limit the technical scope of the present invention.

Figure 1:
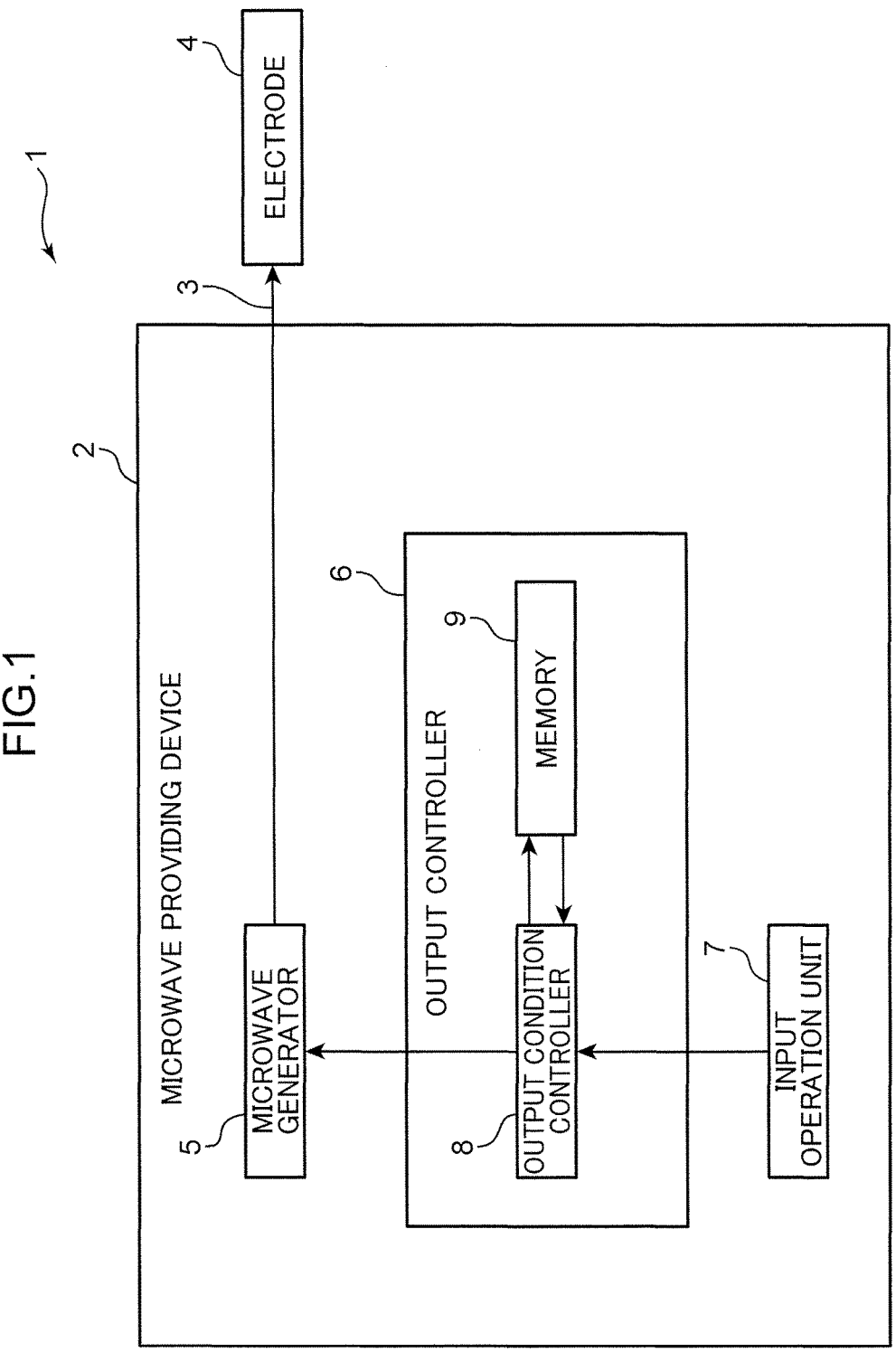
FIG. 1 is a block diagram illustrating a schematic configuration of a microwave surgical device according to an embodiment of the present invention.

Referring to FIG. 1, a microwave surgical device 1 includes a surgical electrode 4, a microwave providing device 2 for providing microwaves to the electrode 4, and a coaxial cable 3 that detachably connects the electrode 4 and the microwave providing device 2.

Figure 9:
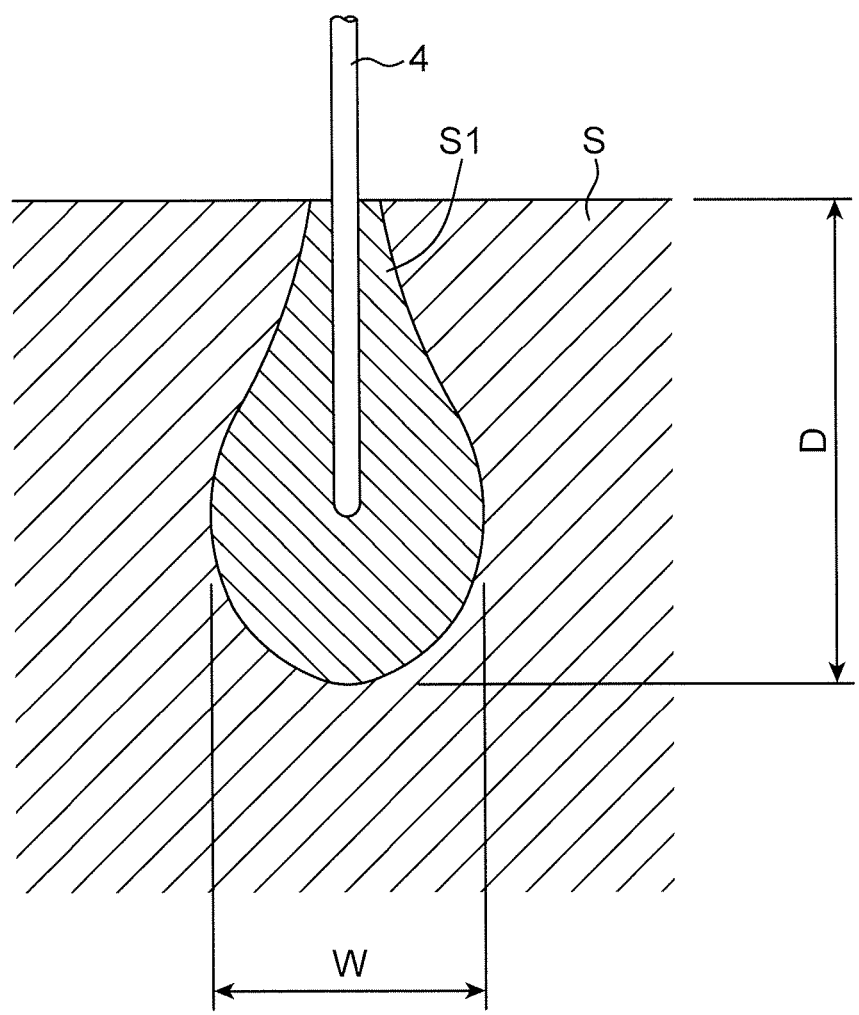
FIG. 9 is a schematic cross-sectional view illustrating a state in which a treatment target tissue is coagulated by the microwave surgical device of FIG. 1.

The electrode 4 is a rod-shaped electrode in which a central electrode and an outer electrode covering the central electrode from the outer side are disposed on the same axis (see FIG. 9). Moreover, a coating (not illustrated) formed of a fluorine resin is formed on an outer circumferential surface of the electrode 4 in order to suppress attachment of a treatment target tissue S.

As illustrated in FIG. 1, the microwave providing device 2 includes a microwave generator 5 for generating microwaves, an output controller 6 that controls the microwave generator 5, and an input operation unit 7 for allowing an operator to input predetermined information.

The microwave generator 5 can generate microwaves of the frequency 2450±50 MHz. A microwave generation mechanism of the microwave generator 5 is not particularly limited.

The output controller 6 controls the microwave generator 5 so that microwaves are generated intermittently. Specifically, the output controller 6 controls the microwave generator 5 so that microwaves are intermittently radiated after cumulative radiation period of microwaves radiated to the treatment target tissue S exceeds predetermined reference cumulative radiation period. Hereinafter, reference cumulative radiation period Ti1 will be described with reference to FIG. 2.

Figure 2:
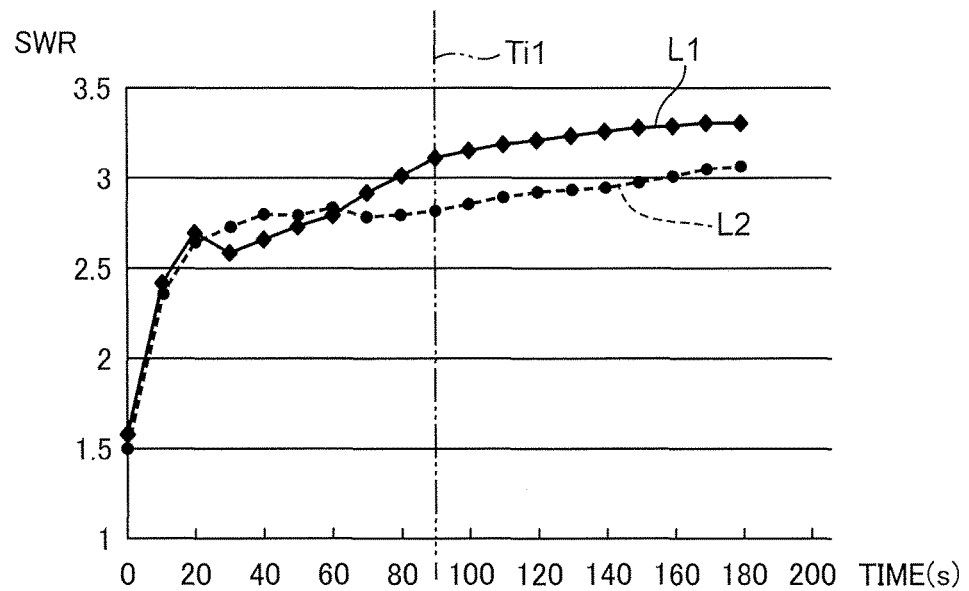
FIG. 2 is a graph illustrating the efficiency of dielectric heating by microwaves.

FIG. 2 is a graph illustrating a standing wave ratio (hereinafter referred to as SWR) with respect to a cumulative radiation period of microwaves to a treatment target tissue (a tissue having approximately the same relative permittivity as the liver) S. The output power of microwaves is 80 W and the frequency thereof is 2450±50 MHz.

In FIG. 2, symbol L1 indicates SWR (second efficiency) when microwaves are radiated continuously and symbol L2 indicates SWR (first efficiency) when microwaves are intermittently radiated with a radiation period of 10 seconds and a pause period of 5 seconds. Moreover, both SWRs L1 and L2 are obtained when microwaves are radiated until the cumulative radiation period of microwaves reaches 180 seconds.

Here, when the amount of moisture in the treatment target tissue S decreases and the load impedance of the treatment target tissue S changes, the SWR increases. That is, the smaller the SWR, the better the efficiency of dielectric heating.

As illustrated in FIG. 2, when the SWR L2 during intermittent radiation is set to $P<0.05$ and the cumulative radiation period exceeds approximately 90 seconds, there is a significant difference between the SWR L1 during continuous radiation and the SWR L2 during intermittent radiation.

Thus, in the microwave surgical device 1, the reference cumulative radiation period Ti1 is set to 90 seconds when the treatment target tissue S subject to treatment is the liver, the microwaves have an output power of 80 W and a frequency of 2450±50 MHz, and the radiation period per each radiation is 10 seconds and the pause period per each pause is 5 seconds.

That is, the output controller 6 illustrated in FIG. 1 controls the microwave generator 5 so that microwaves are intermittently radiated at least after the cumulative radiation period reaches 90 seconds under conditions that the output power is 80 W, the frequency is 2450±50 MHz, the radiation period is 10 seconds, and the pause period is 5 seconds.

Specifically, the output controller 6 includes an output condition controller 8 that controls the output conditions of intermittent radiation of microwaves and a memory 9 that stores a predetermined target radiation count of microwaves.

The output condition controller 8 extracts an appropriate condition among the output conditions stored in advance in the memory 9 according to an operation of the input operation unit 7 and outputs a command to the microwave generator 5 so that microwaves are intermittently radiated under this condition.

For example, when the input operation unit 7 inputs a command that the treatment target tissue S is the liver, the output condition controller 8 sets an output condition that the output power is 80 W, the radiation period is 10 seconds, and the pause period is 5 seconds and outputs a command to the microwave generator 5.

Moreover, the output condition controller 8 controls the number of intermittent radiations of microwaves by referring to the type of the treatment target tissue S input by the input operation unit 7 and the target radiation count stored in the memory 9. Here, the target radiation count which will be described in detail later is the number of intermittent radiations in which the cumulative radiation period of microwaves is equal to or larger than the reference cumulative radiation period Ti1 (90 seconds) and extension of the coagulation range (the range indicated by symbol W in FIG. 9) by intermittent radiation of microwave under the output condition converges (the coagulation range does not extend as expected even if intermittent radiation is performed further).

The reference cumulative radiation period of 90 seconds is a value set depending on the type (a tissue having approximately the same relative permittivity as the liver) of the treatment target tissue S and the output conditions that the output power is 80 W, the frequency of 2450±50 MHz, the radiation period of microwaves is 10 second, and the pause period is 5 seconds. Here, it can be expected that the reference cumulative radiation period Ti1 changes if the radiation period and the pause period change. The following test is performed in order to find better conditions (a radiation period and a pause period) by assuming that, if the reference cumulative radiation period Ti1 is set to 90 seconds or longer, dielectric heating can be performed with higher efficiency than when microwaves are radiated continuously.

The purpose of this test is to specify a condition (a radiation period and a pause period) that maximizes a width dimension W of a coagulation range of the treatment target tissue S by the electrode 4 inserted into the treatment target tissue S as illustrated in FIG. 9. In FIG. 9, symbol D indicates a depth dimension of the treatment target tissue S in a length direction of the electrode 4.

Figure 3:
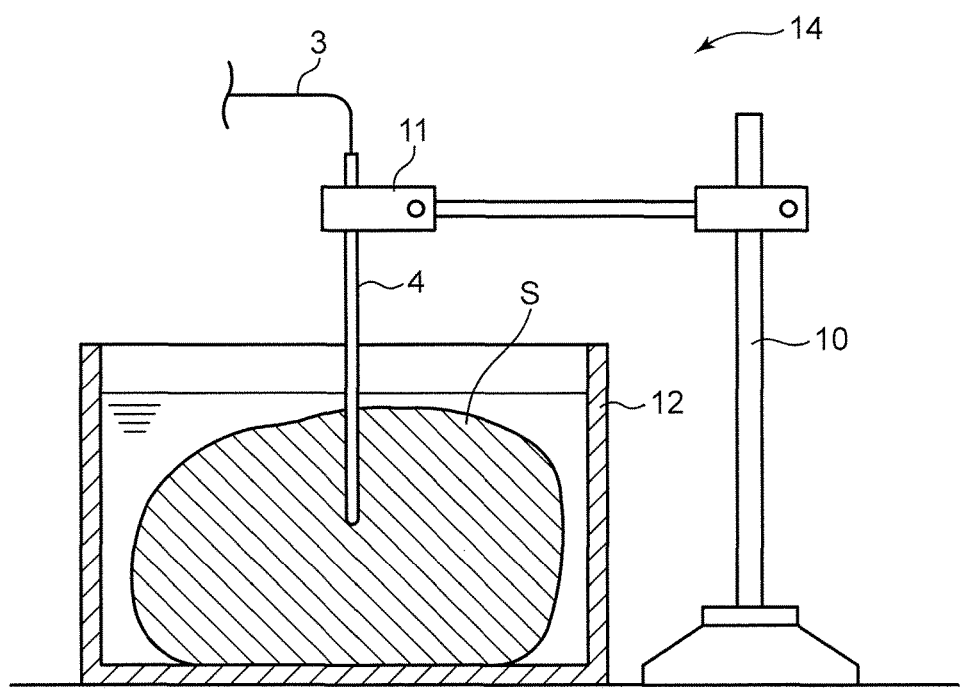
FIG. 3 is a schematic cross-sectional view illustrating a test device used for measurement of the coagulation range of a treatment target tissue.

First, a test device 14 for measuring a coagulation range of the treatment target tissue S will be described with reference to FIG. 3.

The test device 14 includes a water bus 12 for adjusting the treatment target tissue (a tissue having approximately the same relative permittivity as the liver) S to a predetermined temperature, a clamp 11 that holds the electrode 4 with a distal end inserted into the treatment target tissue S, a stand 10 that supports the clamp 11, and a microwave providing device (not illustrated) connected to the electrode 4 by the coaxial cable 3.

The microwave providing device can set a microwave radiation condition (an output power, a frequency, a radiation period, and a pause period) and can provide microwaves to the electrode 4 according to the radiation condition.

The water stored in the water bus 12 is maintained to a predetermined temperature by a heater (not illustrated).

Microwaves are intermittently radiated to the treatment target tissue S via the electrode 4 in a state in which the temperature of the treatment target tissue S in the water bus 12 is stably maintained to a predetermined temperature.

<Test Result 1 (FIG. 4)>

In this test, the coagulation range W is measured for Examples 1 to 9.

In Examples 1 to 3, the radiation period is set to 10 seconds, the pause period is set to 5 seconds, and the total radiation period (cumulative radiation period) is set to 90 seconds for Example 1, 120 seconds for Example 2, and 210 seconds for Example 3.

In Examples 4 to 6, the radiation period is set to 20 seconds, the pause period is set to 5 seconds, and the total radiation period is set to 100 seconds for Example 4, 160 seconds for Example 5, and 220 seconds for Example 6.

In Examples 7 to 9, the pause period is set to 10 seconds, the total radiation period is set to 120 seconds, and the radiation period is set to 10 seconds for Example 7, 15 seconds for Example 8, and 20 seconds for Example 9.

In test result 1, from comparison among Examples 1 to 3 and comparison among Examples 4 to 6, it can be understood that, when the radiation period and the pause period are constant, the coagulation range W increases as the number of repeats increases.

Moreover, from comparison between Examples 1 and 4, comparison between Examples 2 and 5, and comparison between Examples 3 and 6, it can be understood that the coagulation range W when the radiation period is 10 seconds is wider than the coagulation range W when the radiation period is 20 seconds.

When Examples 2 and 9 in which the total radiation period is 120 seconds are compared, although a wider coagulation range W is measured for Example 9, a further test is not performed under a condition of the radiation period of 20 seconds in which the temperature of the electrode 4 is higher than when the radiation period is 10 seconds.

Further, when Examples 7 and 8 in which the pause period is 10 seconds and the total radiation period is 120 seconds are compared, it can be understood that the coagulation range W when the radiation period is 15 seconds is wider than the coagulation range W when the radiation period is 10 seconds.

Thus, the following test is performed in order to check the limit of the coagulation range W when the radiation period is 10 seconds and the pause period is 5 seconds and when the radiation period 15 seconds and the pause period is 10 seconds.

<Test Result 2 (FIGS. 5 and 6)>

As illustrated in FIG. 5, in this test, the coagulation range W is checked for Comparative Examples 1 to 3 and Examples 10 to 19.

In Comparative Examples 1 to 3, the total radiation period is set to 60 seconds, which is shorter than the reference cumulative radiation period Ti1 (90 seconds). In Comparative Example 1, microwaves are radiated continuously. In Comparative Example 2, the radiation period is set to 10 seconds and the pause period is set to 5 seconds. In Comparative Example 3, the radiation period is set to 15 seconds and the pause period is set to 5 seconds.

The pair of Examples 10 and 11, the pair of Examples 12 and 13, the pair of Examples 14 and 15, and the pair of Examples 16 and 17 are pairs of example in which the radiation period is set to 10 seconds and the pause period is set to 5 seconds and example in which the radiation period is set to 15 seconds and the pause period is set to 10 seconds.

The number of repeats is set to 10 for Examples 10 and 11, the number of repeats is set to 15 for Examples 12 and 13, the number of repeats is set to 20 for Examples 14 and 15, and the number of repeats is set to 25 for Examples 16 and 17.

In Examples 18 and 19, the radiation period is set to 10 seconds and the pause period is set to 5 seconds. Moreover, the number of repeats is set to 30 for Example 18 and the number of repeats is set to 35 for Examples 19.

FIG. 6 illustrates Comparative Examples 1 to 3 and Examples 10 to 19 in descending order of the coagulation ranges W.

Referring to FIGS. 5 and 6, it can be understood that there is no great difference in the coagulation ranges W of Comparative Examples 1 to 3. Due to this, it can be understood that there is little influence on the coagulation range W even when microwaves are radiated continuously or intermittently as long as the cumulative radiation period is within the reference cumulative radiation period.

Moreover, Examples 16 and 18 are compared to check the relation between the number of repeats and the coagulation range W. The coagulation range W of Example 18 is smaller than the coagulation range W of Example 16 despite the fact that the number of repeats of Example 18 is larger than the number of repeats of Example 16. Moreover, when Examples 16 and 19 are compared, the coagulation range W of Example 19 is changed only 2 mm from the coagulation range W of Example 16 despite the fact that the number of repeats of Example 19 is larger by 10 than the number of repeats of Example 16. From these facts, the number of repeats (the target radiation count) in which, under the output conditions that the radiation period is 10 seconds, the pause period is 5 seconds, the output power is 80 W, and the frequency is 2450±50 MHz, the extension of the coagulation range converges is set to 25. The target radiation count is stored in the abovementioned memory 9 (see FIG. 1).

Further, Example 19 and Examples 15 and 17 are compared and Examples 13 and 16 are compared to check the relation between the total period and the coagulation range W. From the comparison, it can be understood that the coagulation range W can be extended more efficiently when the total period is set such that the radiation period is 10 seconds and the pause period is 5 seconds than when the radiation period is 15 seconds and the pause period is 10 seconds.

Moreover, Example 16 and Examples 15 and 17 are compared to check the relation between the total radiation period and the coagulation range W. From the comparison, it can be understood that a wide coagulation range W can be obtained in a shorter total radiation period when the radiation period is 10 seconds and the pause period is 5 seconds than when the radiation period is 15 seconds and the pause period is 10 seconds.

From these results, it can be understood that the combination of the radiation period of 10 seconds and the pause period of 5 seconds is better than the combination of the radiation period of 15 seconds and the pause period of 10 seconds.

Here, when the liver of a patient (human body) is coagulated under the condition of Example 14, the measured coagulation value (W×D) is 27 mm×42 mm and the same result as the test is obtained. Moreover, when the liver of a patient (human body) is coagulated under a reference condition that the output power of microwaves is 60 W, the radiation period is 15 seconds, the pause period is 5 seconds, and the number of repeats is 20, the measured coagulation value (W×D) is 25 mm×40 mm.

Thus, the following test is performed by fixing the intermittent radiation period of microwaves to 10 seconds.

<Test Result 3 (FIG. 7)>

In Examples 20 to 22, the radiation period is set to 10 seconds and the number of repeats is set to 30. Moreover, the pause period is set to 5 seconds for Example 20, the pause period is set to 10 seconds for Example 21, and the pause period is set to 15 seconds for Example 22.

Further, in Example 23, microwaves are radiated continuously in the reference cumulative radiation period Ti1 (90 seconds), and microwaves are intermittently radiated after the reference cumulative radiation period Ti1. The radiation period per each intermittent radiation is set to 10 seconds and the pause period is set to 5 seconds.

Moreover, the total radiation period of Examples 20 to 23 is 300 seconds.

From comparison among Examples 20 to 22, it can be understood that, the shorter the pause period, the wider the coagulation range W when the radiation period per each radiation and the total radiation period are constant. This is considered to be attributable to the fact that the shorter the pause period, the better the efficiency of utilizing the increase in the temperature of the treatment target tissue S by previously radiated microwaves.

Figure 8:
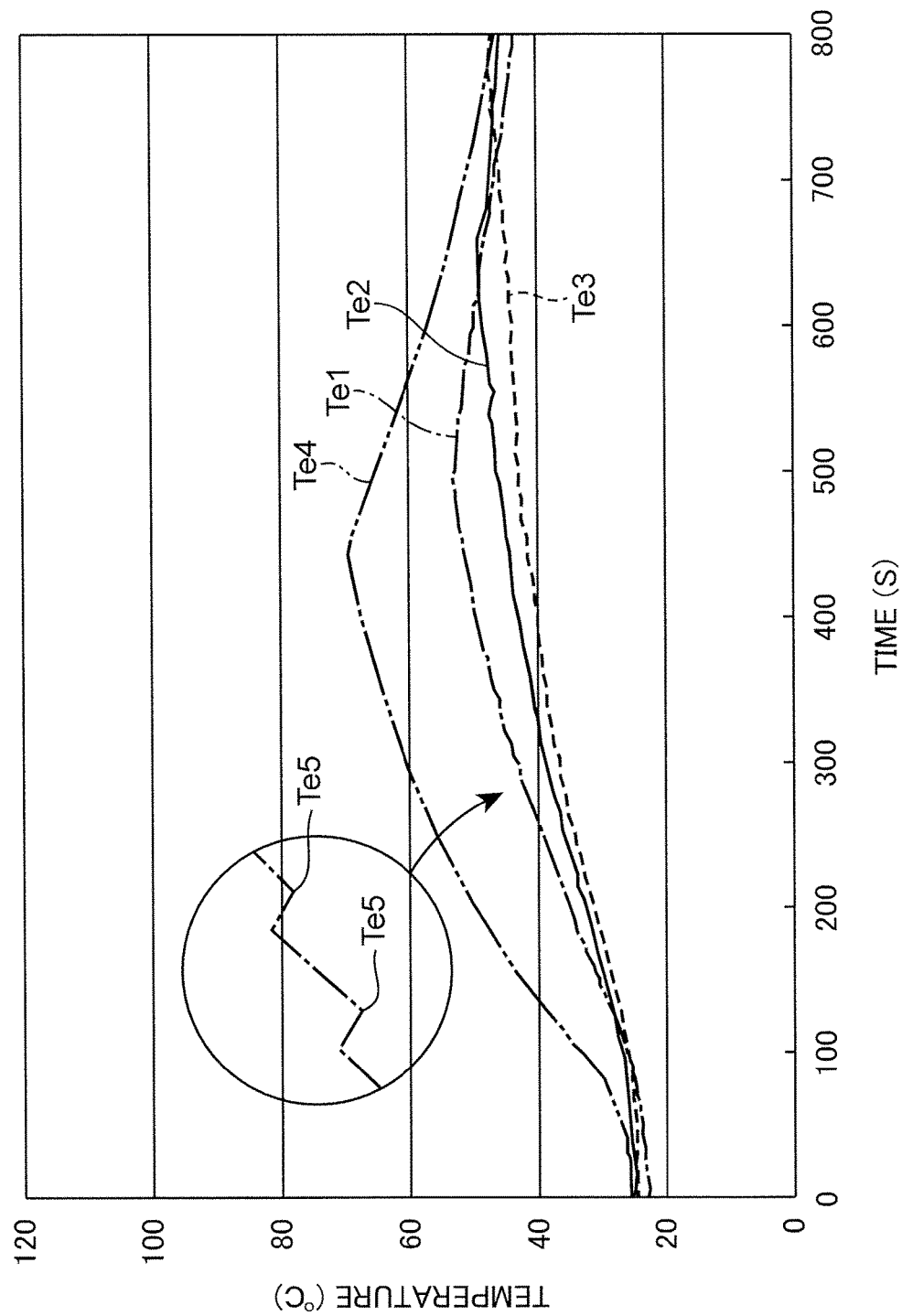
FIG. 8 is a graph illustrating the temperature of a treatment target tissue measured under the conditions corresponding to test result 3 of FIG. 7.

Specifically, as illustrated in FIG. 8, the magnitude of a temperature increase rate (the inclination of the graph) per unit time of the temperature Te1 of the treatment target tissue S for Example 20, the temperature Te2 of the treatment target tissue S for Example 21, and the temperature Te3 of the treatment target tissue S for Example 22 has a relation of Te1>Te2>Te3.

Moreover, as illustrated at an enlarged scale in FIG. 8, in Examples 20 to 22, subsequent microwave radiation is performed before the temperature of a treatment target tissue S increased by the previous microwave radiation decreases. That is, in Examples 20 to 22, an (n+1)th radiation of microwaves is performed after a pause period (5, 10, and 15 seconds) that is shorter than a period in which the temperature of a treatment target tissue S dielectrically heated by an n-th radiation of microwaves decreases to the temperature Te5 at the start time of the n-th radiation of microwaves.

Although the changes in the temperature illustrated in FIG. 8 are measured at a position of the treatment target tissue S distant in the radial direction from the electrode 4, the same temperature changes are observed even when the distance from the electrode 4 is changed.

Moreover, when Examples 20 and 23 are compared, it can be understood that the same coagulation range W is obtained when microwaves are intermittently radiated after the reference cumulative radiation period Ti1 regardless of whether microwaves are radiated continuously (Example 23) within the reference cumulative radiation period Ti1 or not (Example 20).

Moreover, in the temperature graphs Te1 to Te4 of FIG. 8, a turning point at which a characteristic of rising to the right changes to a characteristic of lowering to the right corresponds to substantially the time at which radiation of microwaves ends.

From the above, it is confirmed that, when the treatment target tissue S is a tissue having approximately the same relative permittivity as the liver, and the output power of microwaves is 80 W and the frequency thereof is 2450±50 MHz, the output condition that the radiation period is 10 seconds, the pause period is 5 seconds, and the reference cumulative radiation period is 90 seconds or more is the best condition among test results 1 to 3.

Moreover, it is confirmed that among the radiation condition, the target radiation count in which the extension of the coagulation range converges is 25 as illustrated in Example 16 illustrated in FIGS. 5 and 6.

Further, as in Example 23 of FIG. 7, the same result as the case (Example 20) in which microwaves are radiated intermittently before the reference cumulative radiation period Ti1 is obtained even when microwaves are radiated continuously during the reference cumulative radiation period Ti1 and microwaves are radiated intermittently after the reference cumulative radiation period Ti1. Thus, it is confirmed that radiating microwaves continuously until the reference cumulative radiation period Ti1 is reached is a satisfactory condition as in Example 23.

As described above, as illustrated in FIG. 2, the microwave providing device 2 radiates microwaves intermittently after the reference cumulative radiation period Ti1 of microwaves in which SWR L2 becomes smaller than SWR L1 (the first efficiency becomes larger than the second efficiency). By doing so, dielectric heating by microwaves can be performed with the first efficiency higher than the second efficiency by intermittent radiation of microwaves subsequent to the reference cumulative radiation period Ti1.

Here, the followings are considered as the causes of why the first efficiency becomes larger than the second efficiency (SWR L2 becomes smaller than SWR L1) if the time exceeds the reference cumulative radiation period Ti1.

Such an amount of moisture that does not affect the efficiency of dielectric heating remains around the surgical electrode 4 in the treatment target tissue S until the reference cumulative radiation period Ti1 is reached regardless of continuous radiation and intermittent radiation. On the other hand, when microwaves are radiated continuously over the reference cumulative radiation period Ti1, the amount of moisture around the electrode of the treatment target tissue S decreases due to evaporation to such an amount that the efficiency of dielectric heating decreases. In contrast, when microwaves are radiated intermittently after the reference cumulative radiation period Ti1, although the amount of moisture around the electrode 4 of the treatment target tissue S during radiation of microwaves decreases, moisture returns from the surrounding portion during the pause period of microwave radiation and the efficiency of dielectric heating increases due to the returning moisture.

Thus, as in the present invention, by intermittently radiating microwaves at least after the reference cumulative radiation period Ti1, it is possible to perform dielectric heating with the first efficiency higher than the second efficiency.

Thus, according to the present invention, it is possible to effectively extend the coagulation range using microwaves unlike a case in which microwaves are intermittently radiated during the reference cumulative radiation period Ti1 only.

According to the embodiments, the following advantages are obtained.

The output controller 6 controls the microwave generator 5 so that microwaves are generated intermittently before the reference cumulative radiation period Ti1. Thus, it is possible to simplify the processing as compared to when control of the microwave generator 5 is switched between continuous radiation and intermittent radiation of microwaves.

Moreover, since it is possible to shorten the time per each radiation in which microwaves are continuously provided to the electrode 4, it is possible to suppress resistance heat generated in the electrode 4 to be low. Thus, it is possible to suppress the electrode 4 from being heated to high temperature without providing a structure for cooling the resistance heat generated in the electrode 4.

The output controller 6 stores the target radiation count (25) in advance as the number of microwave radiations in which it is not expected that the coagulation range is extended further and controls the microwave generator 5 so that generation of microwaves stops at the target radiation count. Thus, it is possible to suppress unnecessary radiation of microwaves.

In the embodiment, microwaves are intermittently radiated up to the target radiation count for obtaining the maximum value of the coagulation range W by intermittent radiation of microwaves under specific output conditions. A plurality of target radiation counts for respective target coagulation ranges W may be stored in the memory 9 in advance and the target radiation count may be selected according to the coagulation range W input by the input operation unit 7.

In this case, when the target coagulation range W is input using the input operation unit 7, the output condition controller 8 determines a radiation count corresponding to the input coagulation range W by referring to the memory 9 and outputs a command for performing intermittent radiation of microwaves under the output condition to the microwave generator 5.

Moreover, in the microwave providing device 2, as illustrated in FIG. 8, subsequent microwave radiation is performed before the temperature of a treatment target tissue S increased by the previous microwave radiation decreases. Thus, dielectric heating can be performed by the subsequent radiation of microwaves using the heat generated by the dielectric heating based on the previous radiation of microwaves. As a result, it is possible to efficiently extend the coagulation range while suppressing the influence of the effect (in particular, the cooling effect) of the treatment target tissue S.

The output controller 6 sets the radiation period per each radiation of microwaves to 10 seconds and the pause period to 5 seconds. Thus, a relatively large area (W×D=27 mm×42 mm) of the liver of a human body, for example, can be coagulated.

Moreover, in the embodiment, since a coating for suppressing attachment of the treatment target tissue S is formed on the electrode 4, it is possible to eliminate a special process of supplying dissociation current for suppressing attachment of the treatment target tissue S.

In the embodiment, although the radiation period is set to 10 seconds and the pause period is set to 5 seconds, the radiation period and the pause period are not limited to these values. For example, it is confirmed from tests that a coagulation range similar to the condition of the radiation period of 10 seconds and the pause period of 5 seconds is obtained for a combination (Example 6 of FIG. 4: 28 mm×50 mm) of the radiation period of 20 seconds and the pause period of 5 seconds, a combination (Example 17 of FIG. 5: 31 mm×60 mm) of the radiation period of 15 seconds and the pause period of 10 seconds, and a combination (Example 9 of FIG. 4: 26 mm×50 mm) of the radiation period of 20 seconds and the pause period of 10 seconds. Thus, these combinations can be also employed.

Moreover, as in Example 23 illustrated in FIG. 7, when microwaves are generated continuously until the reference cumulative radiation period Ti1 is reached, it is not necessary to provide the pause period of microwaves until the reference cumulative radiation period is reached. Thus, it is possible to shorten the time required for coagulation of the treatment target tissue S as compared to the case of radiating microwaves always intermittently.

Although the output controller 6 of the embodiment sets the target radiation count in which the cumulative radiation period of microwaves becomes equal to or larger than the reference cumulative radiation period Ti1, radiation of microwaves may not stop at the target radiation count. The output controller 6 may control the microwave generator 5 so that intermittent radiation of microwaves is executed after the reference cumulative radiation period Ti1.

The specific embodiment mainly includes inventions having the following configuration.

In order to solve the problem, the present inventors have invented the present invention by focusing on the fact that first efficiency of dielectric heating by microwaves with respect to a cumulative radiation period of the microwaves intermittently radiated to a treatment target tissue exceeds second efficiency of dielectric heating by microwaves with respect to a cumulative radiation period of microwaves continuously radiated to the treatment target tissue when the cumulative radiation period exceeds a specific period.

Specifically, the present invention provides a microwave providing device for providing microwaves to a surgical electrode, including: a microwave generator that generates the microwaves; and an output controller that controls the microwave generator so that the microwaves are generated intermittently, wherein the output controller controls the microwave generator based on a first efficiency of dielectric heating by microwaves with respect to a cumulative radiation period of microwaves radiated intermittently to a treatment target tissue and a second efficiency of dielectric heating by microwaves with respect to a cumulative radiation period of microwaves radiated continuously to the treatment target tissue so that microwaves are intermittently radiated at least after a reference cumulative radiation period that is set in advance as a cumulative radiation period at which the first efficiency becomes larger than the second efficiency.

In the present invention, microwaves are radiated intermittently after the reference cumulative radiation period of microwaves at which the first efficiency becomes larger than the second efficiency. Due to this, by intermittent radiation of microwaves after the reference cumulative radiation period, it is possible to perform dielectric heating by microwaves with the first efficiency higher than the second efficiency.

Here, the following are considered as the causes of why the first efficiency becomes larger than the second efficiency if the time exceeds the reference cumulative radiation period.

Such an amount of moisture that does not affect the efficiency of dielectric heating remains around the surgical electrode in the treatment target tissue until the reference cumulative radiation period is reached regardless of continuous radiation and intermittent radiation. On the other hand, when microwaves are radiated continuously over the reference cumulative radiation period, the amount of moisture around the electrode of the treatment target tissue decreases due to evaporation to such an amount that the efficiency of dielectric heating decreases. In contrast, when microwaves are radiated intermittently after the reference cumulative radiation period, although the amount of moisture around the electrode of the treatment target tissue during radiation of microwaves decreases, moisture returns from the surrounding portion during the pause period of microwave radiation and the efficiency of dielectric heating increases due to the returning moisture.

Thus, as in the present invention, by intermittently radiating microwaves at least after the reference cumulative radiation period, it is possible to perform dielectric heating with the first efficiency higher than the second efficiency.

Thus, according to the present invention, it is possible to effectively extend the coagulation range using microwaves unlike a case in which microwaves are intermittently radiated during the reference cumulative radiation period only.

The first efficiency, the second efficiency, and the reference cumulative radiation period are determined according to the output power and the frequency of microwaves, the type (a difference between relative permittivities) of the treatment target tissue, and the radiation period and the pause period of microwaves.

In the microwave providing device, it is preferable that the output controller controls the microwave generator so that microwaves are generated intermittently also before the reference cumulative radiation period.

According to this aspect, it is possible to simplify the processing as compared to when control of the microwave generator is switched between continuous radiation and intermittent radiation of microwaves.

Moreover, in the aspect, since it is possible to shorten the time per each radiation in which microwaves are continuously provided to the electrode, it is possible to suppress resistance heat generated in the electrode to be low. Thus, it is possible to suppress the electrode from being heated to high temperature without providing a structure for cooling the resistance heat generated in the electrode.

In the microwave providing device, it is preferable that the output controller controls the microwave generator so that microwaves are generated continuously until the reference cumulative radiation period is reached.

According to this aspect, since it is not necessary to provide the pause period of microwaves until the reference cumulative radiation period is reached, it is possible to shorten the time required for coagulation of the treatment target tissue as compared to the case of radiating microwaves always intermittently.

In the microwave providing device, it is preferable that the output controller stores in advance a target radiation count, in which a coagulation range of the treatment target tissue becomes a predetermined target range, and controls the microwave generator so that generation of microwaves stops at the target radiation count.

According to this aspect, it is possible to automatically stop generation of microwaves at the target radiation count for realizing a target coagulation range.

Here, it is confirmed that the coagulation range of the treatment target tissue is not further extended if the cumulative radiation period of microwaves exceeds a specific period. Thus, it is possible to suppress unnecessary radiation of microwaves when the number of radiations for obtaining a cumulative radiation period, in which extension of the coagulation range is not expected any further, is set to the target radiation count.

The target radiation count can be set in advance according to the output power and the frequency of microwaves, the type of the treatment target tissue, and the radiation period and the pause period of microwaves.

In the microwave providing device, it is preferable that the output controller controls the microwave generator so that an (n+1)th radiation of microwaves is performed after a pause period that is shorter than a period in which a temperature of the treatment target tissue dielectrically heated by an n-th radiation of microwaves decreases to a temperature at the start time of the n-th radiation of microwaves.

With regard to the returning phenomenon of the moisture in the treatment target tissue, it is considered that the longer the pause period provided between the intermittent radiation periods of microwaves, the more advantageous to dielectric heating. On the other hand, it is confirmed that, when the radiation period per each radiation of microwaves is fixed, the longer the pause period, the narrower the coagulation range of the treatment target tissue. This is considered to be attributable to the fact that the treatment target tissue is cooled in the pause period by the influence of an ambient temperature or the circulation of the blood or the like of a living body. In particular, it is considered that the effect of cooling the treatment target tissue by the circulation of the blood or the like (hereinafter referred to as a cooling effect) has the major influence.

Thus, as in the aspect, when subsequent microwave radiation is performed before the temperature of the treatment target tissue increased by the previous microwave radiation decreases, dielectric heating can be performed by the subsequent radiation of microwaves using the heat generated by the dielectric heating based on the previous radiation of microwaves. As a result, it is possible to efficiently extend the coagulation range while suppressing the influence of the effect (in particular, the cooling effect) of cooling the treatment target tissue.

It is necessary to change the radiation period and the pause period of microwaves appropriately according to the type or the like of the treatment target tissue. For example, when the microwaves have a frequency of 2450±50 MHz, the output controller may set an output power of the microwaves to 80 W, set a radiation period for each radiation of microwaves to 10 seconds, and set a pause period to 5 seconds.

It is confirmed that, by doing so, a relatively large area of the liver of a human body, for example, can be coagulated.

The present invention also provides a microwave surgical device including: a surgical electrode; and the microwave providing device for supplying microwaves to the electrode.

In the microwave surgical device, it is preferable that a coating for suppressing attachment to the treatment target tissue is formed on the surgical electrode.

According to this aspect, a special process of supplying dissociation current for suppressing attachment of the treatment target tissue to the electrode is not required additionally to microwaves for coagulation.

The invention claimed is:

1. A microwave providing device for providing microwaves to a surgical electrode, comprising:
   a microwave generator that generates the microwaves; and
   an output controller that controls the microwave generator so that the microwaves are generated intermittently, wherein:
   the output controller controls the microwave generator based on a first efficiency of dielectric heating by microwaves with respect to a cumulative radiation period of microwaves radiated intermittently to a treatment target tissue under a predetermined first radiation condition and a second efficiency of dielectric heating by microwaves with respect to a cumulative radiation period of microwaves radiated continuously to the treatment target tissue under a predetermined second radiation condition so that microwaves are continuously radiated under the second radiation condition until a reference cumulative radiation period over zero seconds that is set in advance as a cumulative radiation period at which the first efficiency becomes larger than the second efficiency is reached, and so that microwaves are intermittently radiated under the first radiation condition after the reference cumulative radiation period;

the first radiation condition and the second radiation condition include a type of the treatment target tissue, and an output power and frequency of microwaves, and the first radiation condition includes a radiation period of microwaves for one radiation and a pause period of microwaves for one pause.

2. The microwave providing device according to claim 1, wherein the output controller stores in advance a target radiation count, in which a coagulation range of the treatment target tissue becomes a predetermined target range, and controls the microwave generator so that generation of microwaves stops at the target radiation count.

3. The microwave providing device according to claim 1, wherein the output controller controls the microwave generator so that an (n+1)th radiation of microwaves is performed after a pause period that is shorter than a period in which a temperature of the treatment target tissue dielectrically heated by an n-th radiation of microwaves decreases to a temperature at the start time of the n-th radiation of microwaves.

4. The microwave providing device according to claim 1, wherein when the microwaves have a frequency of 2450±50 MHz, the output controller sets an output power of the microwaves to 80 W, sets a radiation period for each radiation of microwaves to 10 seconds, and sets a pause period to 5 seconds.

5. A microwave surgical device comprising:

a surgical electrode; and the microwave providing device according to claim 1, supplying microwaves to the electrode.

6. The microwave surgical device according to claim 5, wherein a coating for suppressing attachment to the treatment target tissue is formed on the surgical electrode.

7. The microwave surgical device according to claim 1, wherein the reference cumulative radiation period is longer than the radiation period of microwaves for one radiation.

8. The microwave surgical device according to claim 1, wherein the reference cumulative radiation period is longer than the radiation period of microwaves for one radiation and the pause period of microwaves for one pause.

* * * * *